(12) United States Patent
Bareket et al.

(10) Patent No.: US 7,483,133 B2
(45) Date of Patent: Jan. 27, 2009

(54) MULTIPLE ANGLE OF INCIDENCE SPECTROSCOPIC SCATTEROMETER SYSTEM

(75) Inventors: Noah Bareket, Saratoga, CA (US); Haiming Wang, Fremont, CA (US)

(73) Assignee: KLA-Tencor Technologies Corporation., Milpitas, CA (US)

( * ) Notice: Subject to any disclaimer, the term of this patent is extended or adjusted under 35 U.S.C. 154(b) by 394 days.

(21) Appl. No.: 11/078,572

(22) Filed: Mar. 11, 2005

(65) Prior Publication Data

US 2006/0126079 A1    Jun. 15, 2006

Related U.S. Application Data

(60) Provisional application No. 60/635,305, filed on Dec. 9, 2004.

(51) Int. Cl.
  *G01J 3/28*    (2006.01)
  *G01J 3/42*    (2006.01)
  *G01J 3/427*    (2006.01)
  *G01B 11/14*    (2006.01)
  *G01B 11/04*    (2006.01)
  *G01B 11/08*    (2006.01)

(52) U.S. Cl. .................... 356/326; 356/319; 356/625; 356/636

(58) Field of Classification Search .......... None
  See application file for complete search history.

(56) References Cited

U.S. PATENT DOCUMENTS 4,548,506 A   10/1985   Elson

| | | |
|---|---|---|
| 5,166,752 A | 11/1992 | Spanier et al. |
| 5,563,702 A | 10/1996 | Emery et al. |
| 5,596,406 A | 1/1997 | Rosencwaig et al. |
| 5,889,593 A | 3/1999 | Bareket |
| 5,910,842 A | 6/1999 | Piwonka-Corle et al. |
| 6,483,580 B1 | 11/2002 | Xu et al. |
| 6,654,131 B2 | 11/2003 | Opsal et al. |
| 6,657,736 B1 * | 12/2003 | Finarov et al. ............ 356/625 |
| 6,721,691 B2 * | 4/2004 | Bao et al. .................... 702/189 |
| 6,778,911 B2 | 8/2004 | Opsal et al. |
| 6,785,638 B2 | 8/2004 | Niu et al. |
| 6,804,005 B2 * | 10/2004 | Bischoff et al. ............ 356/369 |

(Continued)

FOREIGN PATENT DOCUMENTS

WO    WO 99/45340    9/1999

OTHER PUBLICATIONS

Dale M. Byrne and Duncan L. MacFarlane, "Angular Scanning Mechanism for Ellipsometers", Applied Optics, Nov. 1, 1991, vol. 30, No. 31, pp. 4471-4473.

(Continued)

*Primary Examiner*—Gregory J Toatley, Jr.
*Assistant Examiner*—Gordon J Stock, Jr.
(74) *Attorney, Agent, or Firm*—Weaver Austin Villeneuve & Sampson LLP

(57) ABSTRACT

Techniques for optimizing the sensitivity of spectroscopic measurement techniques with respect to certain profile variables by selecting desired measurement angles since the measurement sensitivity to each variable depends, at least in part, on the measurement angles of an incident beam. The selected desired set of measurement angles includes both an azimuth angle and a polar angle. Optimizing the sensitivity of spectroscopic measurement techniques can also reduce or eliminates measurement correlation among variable to be measured.

21 Claims, 7 Drawing Sheets

U.S. PATENT DOCUMENTS

| | | | |
|---|---|---|---|
| 6,856,408 B2 * | 2/2005 | Raymond | 356/601 |
| 7,106,459 B2 * | 9/2006 | Chu | 356/625 |
| 7,126,700 B2 * | 10/2006 | Bao et al. | 356/625 |
| 7,274,472 B2 * | 9/2007 | Bischoff | 356/635 |
| 7,292,335 B2 * | 11/2007 | Brill et al. | 356/319 |
| 7,321,433 B2 * | 1/2008 | Larsen et al. | 356/601 |
| 2002/0033954 A1 * | 3/2002 | Niu et al. | 356/601 |
| 2002/0113966 A1 | 8/2002 | Shchegrov et al. | |
| 2003/0200063 A1 * | 10/2003 | Niu et al. | 703/2 |
| 2004/0017574 A1 | 1/2004 | Vuong et al. | |

OTHER PUBLICATIONS

Woollam et al., "Overview of Variable Angle Spectroscopic Elliposometry (VASE), Part I: Basic Theory and Typical Applications", Proceedings of a conference held Jul. 18-19, 1999, Critical Reviews of Optical Science and Technology, vol. CR72.

Johs et al., "Overview of Variable Angle Spectroscopic Ellipsometry (VASE), Part II: Advanced Applications", Proceedings of a conference held Jul. 18-19, 1999, Critical Reviews of Optical Science and Technology, vol. CR72.

International Search Report dated Oct. 25, 2006, received in corresponding PCT Application No. PCT/US05/44075.

* cited by examiner

MULTIPLE ANGLE OF INCIDENCE SPECTROSCOPIC SCATTEROMETER SYSTEM

CROSS REFERENCE TO RELATED PATENT APPLICATION

This application claims priority of U.S. Provisional Patent Application No. 60/635,305, entitled MULTIPLE ANGLE OF INCIDENCE SPECTROSCOPIC SCATTEROMETER SYSTEM, filed 9 Dec. 2004 by Noah Bareket, et al., which application is incorporated herein by reference in its entirety for all purposes.

FIELD OF THE INVENTION

The present invention relates generally to spectroscopic measurement techniques, and more specifically to using the angle of incidence to increase the sensitivity to profile variables of a sample.

BACKGROUND

Generally the sensitivity of spectroscopic reflectometry and ellipsometry (SE) systems to certain variables of a sample under test is closely related to the angle of incidence (AOI) of the incident beam falling onto the sample. Current SE systems are configured with fixed angles of incidence. One typical SE system measures the thickness of a thin silicon oxide ($SiO_2$, or "oxide" as it is commonly termed) film on a silicon substrate. The sensitivity to the oxide thickness is maximized when the AOI is set close to the Brewster angle of the silicon substrate. This leads to design of SE systems with an AOI at approximately 71 degrees, which has been an optimized system setup for most film measurement applications.

The second angle of the incident beam in a SE system that determines the measurement condition is the azimuthal angle. This angle, which is defined in the plane of the sample, has no impact on measuring film properties. It has an impact, however, when the sample is a feature, not a thin film. Recently SE systems are also used for measuring line profile of periodic features, and the choice of azimuthal angle has become significant. Several SE systems for measuring line profile or periodic structures are described further in U.S. Pat. No. 6,483,580 by Xu et. al, entitled "Spectroscopic Scatterometer System."

In some SE systems, there will be measurement correlation among some critical dimension (CD) variables. Correlation refers to similarities in measurement results that are collected from two different features (or -CD's) within a measured specimen. The similarity causes difficulty in distinguishing and thereby collecting useful information regarding each feature. For example, correlation of measurement results can manifest itself between the measurements of a top and a third-oxide layer in an oxide/nitride/oxide (ONO) film stack. In another example, correlation of measurement results occurs when measuring the height of gratings or contacts and the thickness of one or more underlayers.

One current technique for optimizing an SE system's sensitivity to profile variables and reducing correlation between two CDs or film variables involves fixing one of the variables while the other variable is allowed to float to fit the measured spectral data. However, this technique does not effectively reduce correlation because one cannot know the exact value of the variables to be fixed. As a result, all the variations in these two variables are wrapped into the variable that is allowed to float, which leads to an inaccurate measurement.

Some SE systems can use varying angles of incidence, however none of these systems are applicable to critical dimension measurements. For example, one simple SE system design involves changing both the direction of an incident beam and a collection beam simultaneously. Such systems use a "2-θ" scanning scheme is based on a simple synchronized rotating element that adjusts both the incident beam and the collection beam. J. A. Wollam Co., Inc. has a series of products based on this scheme, which are termed as VASE® (Variable Angle Spectroscopic Ellipsometry).

A modified version of the "2-θ" scanning scheme is described in "Angular Scanning Mechanism for Ellipsometers," by D. M. Byrne and D. L. MacFarlane, Applied Optics, 30(31), 4471-4473, (1991), in which two flat turning mirrors are used to change the angle of the incident beam and the reflection beam simultaneously. A significant drawback of this scheme is the requirement of two synchronized rotations. As the technology node continuously decreases, heading to 45 nm and lower, the performance requirements for metrology tools are also getting higher and higher. To meet leading-edge specifications of precision, accuracy, and tool-to-tool matching for CD measurements, it is critical to calibrate system parameters accurately and maintain a high level of stability for these parameters during measurements. The AOI is one of these critical system parameters that should be exactly calibrated and stabilized. The above VASE design, as a result of two rotating elements, is difficult to calibrate and has difficulty maintaining its AOI. This is the major hurdle preventing the above VASE design from being adopted in semiconductor production lines. As a result, the main applications of systems based on this scheme are typically found in research labs. Again, note that this technology has not been applied to CD measurements. Actually, the drawback of two synchronized mirror rotations would make this scanning scheme particularly difficult to implement for CD measurements.

Another SE system that varies its AOI uses an aperture that is placed in front of a collection mirror. The aperture moves linearly (for example, up and down) to select the desired AOI. The SE system is very simple since only linear movement is required. However, since the aperture allows only a portion of the illumination light to be collected, this system has very low power utilization efficiency.

Another method suggested in U.S. Pat. No. 5,166,752 (the '752 patent) uses a two-dimensional imaging array in combination with a dispersion element (such as a grating or a prism, for instance) to record signals. The measurement columns correspond to signals with a fixed wavelength but varying AOIs, while the measurement rows correspond to signals with a fixed AOI but varying wavelengths. So a pixel in a specific row and a specific column will theoretically pick only signals of a specific wavelength and a specific AOI. One significant problem related to this scheme is described in FIG. 1 of U.S. Pat. No. 5,596,406 (the '406 patent). Briefly, the problem stems from the finite size of the illumination and reflection beam. The problem is that a pixel in a specific row and column will not only record the signal corresponding to the wavelength and AOI specified by the column number and row number, but the signal from adjacent wavelength and AOI may also fall onto this pixel, thereby degrading both the spectral and the angular resolutions.

To overcome the above problem, '406 patent suggests the use of a rectangular aperture, which is elongated in one direction and placed in front of the dispersion element. In this way, only signals corresponding to the azimuth angle parallel to the long-direction of the aperture is allowed to be picked up, which reduces the three dimensional data cube (AOI, azimuth angle, wavelength) into a two dimensional "data plane" (AOI, wavelength). As a result, this scheme effectively eliminates the resolution degradation problem in the '752 patent. Unfortunately, it creates its own problem, namely, the light power utilization is much lower because only a small portion of light corresponding to a given azimuth angle is collected.

In view of the foregoing, there are continuing efforts to provide improved spectroscopic reflectometry and ellipsometry systems that are sensitive to certain profile variables, and which can reduce the measurement correlation between different critical dimensions.

BRIEF SUMMARY OF THE INVENTION

The present invention pertains to optimizing the sensitivity of spectroscopic measurement techniques with respect to certain profile variables by selecting a set of desired measurement angles since the measurement sensitivity to each variable depends, at least in part, on the measurement angles of an incident beam. Sensitivity of spectrometers to certain critical dimension variables varies between applications and depends upon the measurement angles at which an incident beam is oriented. The set of measurement angles include both an azimuth angle and a polar angle. Optimizing the sensitivity of spectroscopic measurement techniques can also reduce or eliminates measurement correlation among variables to be measured.

As a method, one embodiment of the present invention includes at least defining a spectroscopic measurement model of the sample, determining a set of desired measurement angles for a spectroscopic measurement system using the spectroscopic measurement model, directing an incident beam of the spectroscopic system towards a sample at the desired measurement angles, wherein a diffraction beam is diffracted from the sample in response to the incident beam, and extracting the desired measured parameters from the diffracted beam.

As a spectroscopic measurement system, one embodiment of the present invention includes at least a spectroscopic measurement model of a sample, a first analysis module that is arranged to use the spectroscopic measurement model to determine a set of desired measurement angles for the spectroscopic measurement system, an incident beam generator arranged to direct an incident beam towards the sample at the desired measurement angles, wherein a diffracted beam is diffracted from the sample in response to the incident beam, and a plurality of detectors arranged to measure the diffracted beam.

These and other features and advantages of the present invention will be presented in more detail in the following specification of the invention and the accompanying figures, which illustrate by way of example the principles of the invention.

BRIEF DESCRIPTION OF THE DRAWINGS

The invention, together with further advantages thereof, may best be understood by reference to the following description taken in conjunction with the accompanying drawings in which.

DETAILED DESCRIPTION OF THE INVENTION

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known operations have not been described in detail so not to unnecessarily obscure the present invention.

The present invention pertains to techniques for determining a set of desired measurement angles for detecting defects using spectroscopic measurement systems. An incident beam is directed towards a sample at the determined measurement angles, for example, the most sensitive measurement angles, to obtain highly accurate data relating to features upon the sample. A spectroscopic measurement model can be used to model the spectral diffraction profile from the sample at various measurement angles to determine the desired set of measurement angles. A set of measurement angles includes both an azimuth angle and a polar angle.

An incident beam can be various types of beams generated by spectroscopic reflectometry and ellipsometry (SE) systems, which cause spectral diffraction from a sample. For example, the incident beam can be a light beam of various wavelengths or a single wavelength light beam (e.g., a laser), or a group of single wavelength light beam combined into one single beam (e.g., via a beam splitter or a set of beam splitters).

Figure 1:
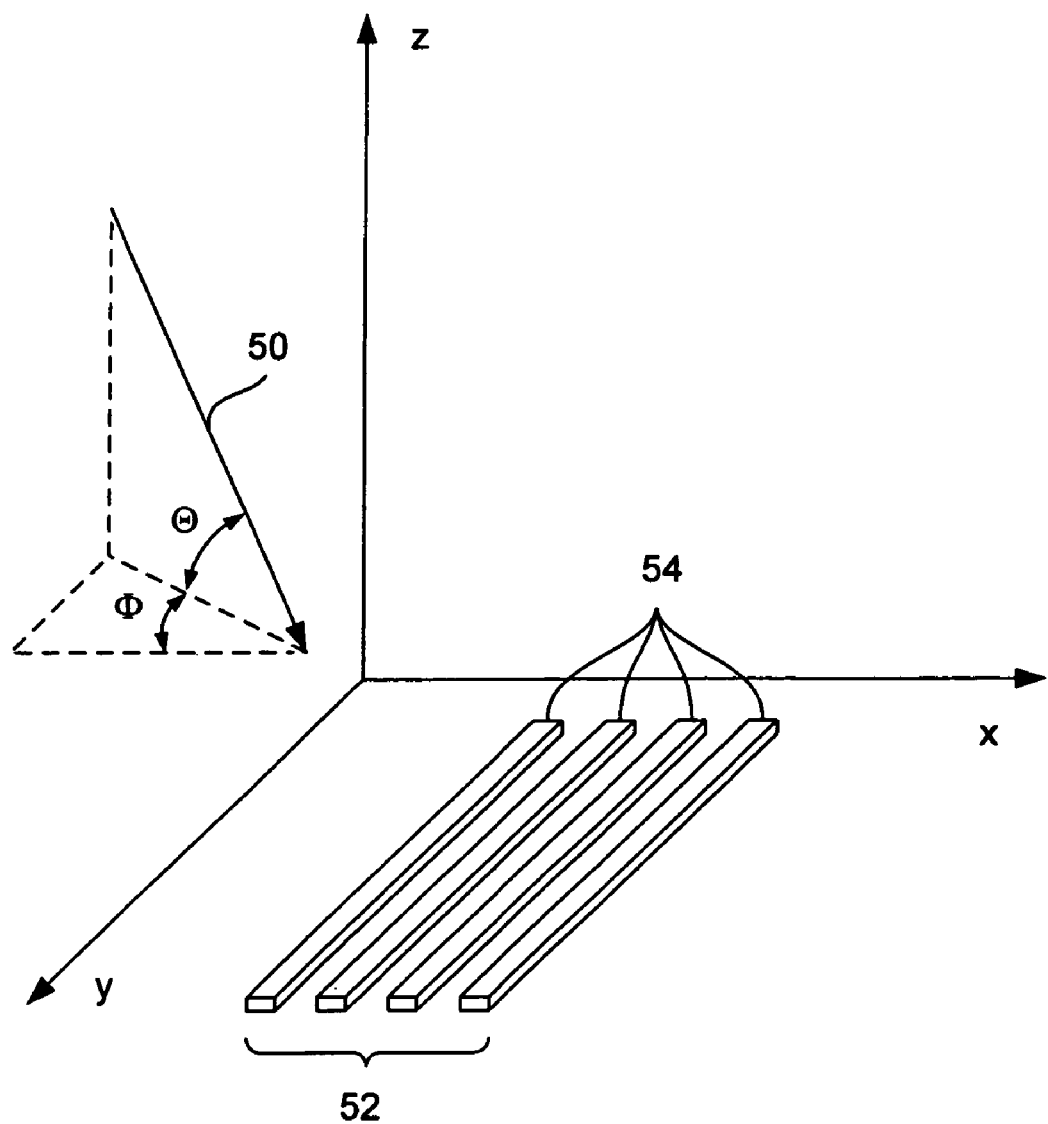
FIG. 1 illustrates a diagrammatic view of an incident beam of a spectroscopic reflectometry and ellipsometry (SE) system, which is directed towards a grating pattern at a particular set of measurement angles.

FIG. 1 illustrates a diagrammatic view of an incident beam 50 of a spectroscopic reflectometry and ellipsometry (SE) system, which is directed towards a grating pattern 52 at a particular set of measurement angles. The grating pattern 52 is formed upon a sample surface. The incident beam 50 and the grating pattern 52 are shown with respect to an orthogonal x-y-z reference system. Incident beam 50 causes spectral diffraction from the sample, which can be detected by spectroscopic detectors (not shown), and then evaluated to determine the value of sample variables. The incident beam 50 may cause one or more beams to be diffracted from the specimen.

The incident beam 50 is tilted at a set of measurement angles that is made up of two components: an azimuth angle, $\Phi$, and a polar angle, $\theta$. The azimuth angle, $\Phi$, is the component of the measurement angle set that is defined within the horizontal plane, which is also the x-y plane. The polar angle, θ, is the angle at which the measurement beam 50 is inclined in the vertical direction relative to the horizontal plane.

In the embodiment of FIG. 1, the grating pattern 52 is formed of a set of raised and parallel lines 54. The grating pattern 52 can be formed on a top surface of a sample or on an underlying layer, which lies beneath the top surface. In some embodiments, grating patterns formed on underlying layers can be perceived through the top layer since the top layer conforms to the shape of the underlying layer. The grating pattern 52 can assist in determining alignment errors between various substrate layers that form a sample, such as a semiconductor wafer. The grating pattern 52 can also be used to measure overlay of two or more layers formed in semiconductor processes.

In alternative embodiments, the incident beam 50 can also be directed upon other features of a sample, such as a semiconductor wafer. Such features can include trenches, vias, or any complex, non-periodic pattern structures found in product wafers. Variables of a feature (or of a grating pattern) for measurement can include, but are not limited to, a middle critical dimension (MCD) or a sidewall angle (SWA), height, an underlayer thickness, a grating/contact height (HT), and other profile variables.

The beam that is diffracted from the sample may vary with the measurement angles 50 of the incident beam and certain measurement angles may cause a peak amount of energy in the diffracted beam. The peak amount of energy corresponds to peak spectral measurements. In some embodiments, the spectral measurement is referred to as being in resonance when peak spectral readings emanate from the sample. Peak energy amounts correspond to highly sensitive measurement conditions, which facilitate the ability to reduce measurement correlation between two variables of interest.

Figure 2:
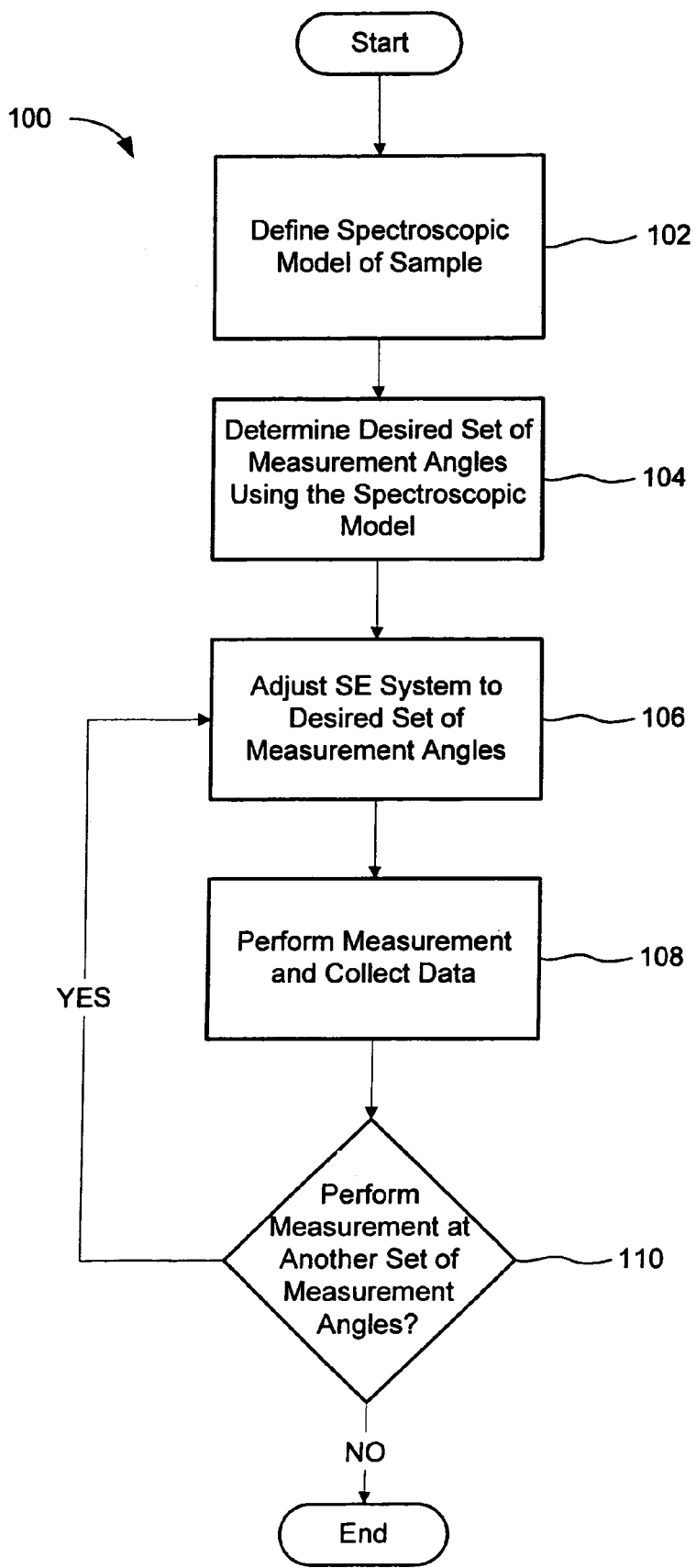
FIG. 2 illustrates a flow chart that describes a process for determining a set of desired measurement angles for an SE system according to one embodiment of the present invention.

FIG. 2 illustrates a flow chart that describes a process 100 for determining a set of desired measurement angles for an SE system according to one embodiment of the present invention. The process 100 can be performed to determine a desired set of measurement angles for one or more sample variables of a sample to be measured. The process 100 begins at operation 102 where a spectroscopic model of a sample is defined. The spectroscopic model is a model that generates theoretical diffraction spectrums that would emanate from a sample in response to an incident beam.

At the next operation 104, the spectroscopic model is utilized to determine a set of desired measurement angles for one or more sample variables. Operation 106 then adjusts the set of measurement angles of an incident beam of an actual SE system to the desired angle found in operation 104. At operation 108, the SE system measures a variable of interest on the sample and collects the spectral diffraction data. At decision block 110, a decision is made as to whether a measurement should be made at an additional set of measurement angles. If yes, then execution of the process 100 returns to operation 106 where the set of measurement angles of the incident beam is readjusted. The new set of measurement angles may be a set of desired angles for a different variable of the sample to be measured. If no additional measurements are to be made, then the process 100 terminates.

With respect to operation 102, the spectroscopic model is, for example, a software model that models how a specific sample would produce a light diffracted from the sample in response to an incident beam. The spectroscopic model of the sample is defined when the model is tailored according to specific parameters that are representative of a sample to be measured by an SE system. In operation 102, the process of defining the spectroscopic model includes defining the values of certain variables within the model. Again, such variables can include, but are not limited to, the height, width, sidewall angles, and diameters of features of interest. Other parameters that should be defined include, but are not limited to, optical properties of the sample, properties of the incident beam, and underlying layer dimensions and properties.

A defined spectroscopic model can then receive input values representative of an incident beam and generate a theoretical diffraction spectrum. The input values relevant to the incident beam may relate to the type of beam involved with the SE system, the current level of the beam, the spot size of the beam, the azimuthal angle of the beam, the polar angle of the beam, and the aperture sizes of the beam ("Numerical Aperture, or NA") in both the azimuth and polar directions. As will now be described, the spectroscopic model is used in operation 104 to determine a set of desired measurement angles.

Figure 3:
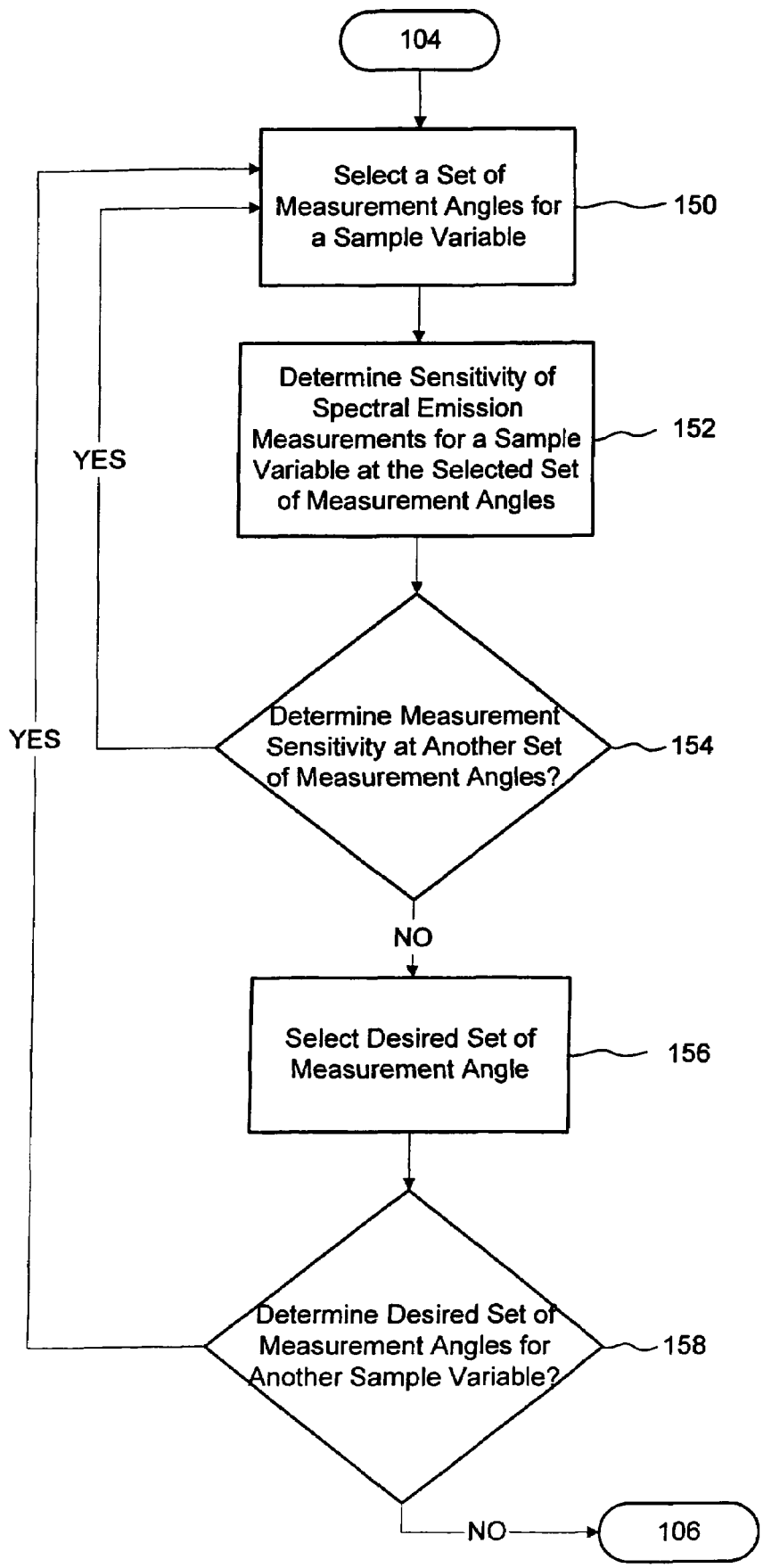
FIG. 3 is a flowchart illustrating the operation of FIG. 2 for determining the measurement angles of the incident beam using a model in accordance with one embodiment of the present invention.

FIG. 3 is a flowchart illustrating the operation 104 of FIG. 2 for determining the measurement angles of the incident beam in accordance with one embodiment of the present invention. Operation 104 determines a set of desired measurement angles for a specific sample variable of interest. For instance, the set of desired measurement angles produces the most sensitive measurement results.

The first sub-operation 150 of operation 104 involves selecting a set of measurement angles at which an incident beam can be directed upon a sample. A set of measurement angles includes a combination of an azimuthal angle and a polar angle; therefore, each component of the set of measurement angles should be selected.

Figure 4:
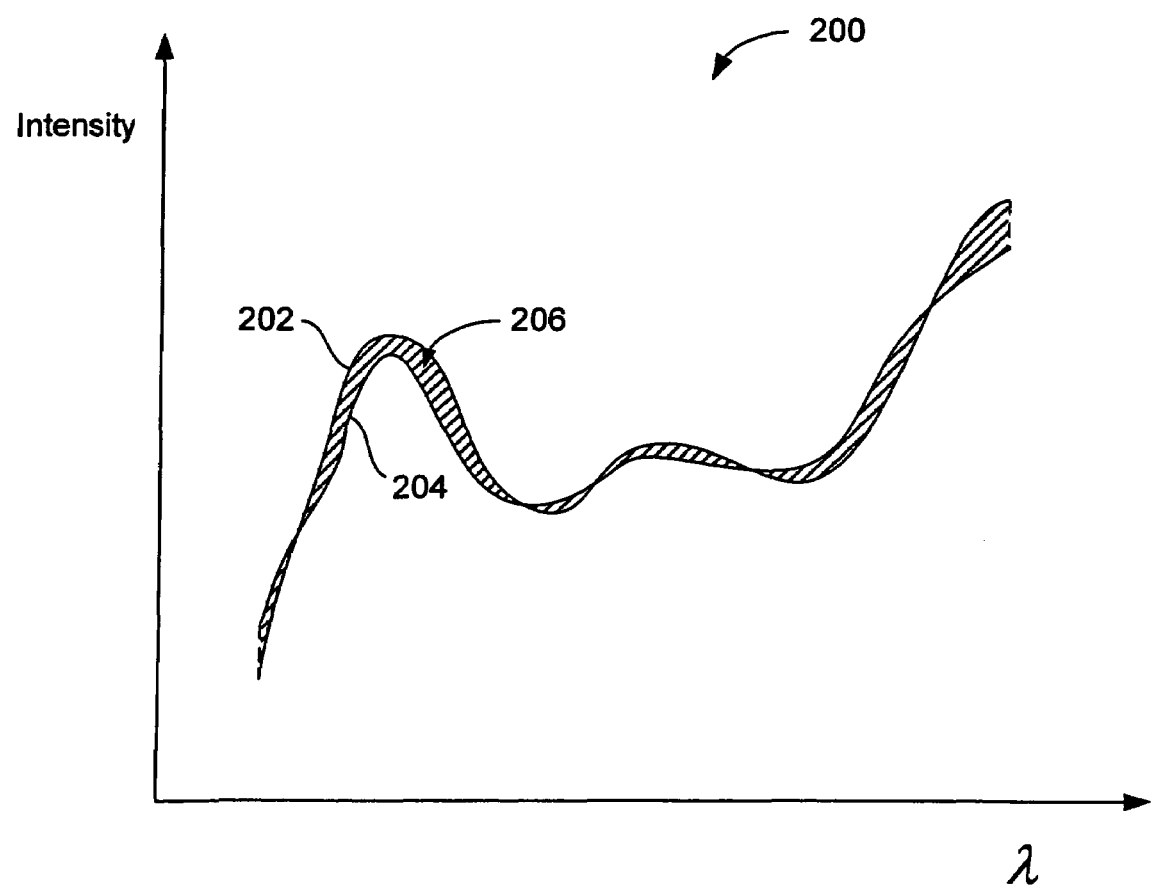
FIG. 4 illustrates a two-dimensional coordinate system that contains two theoretical spectral diffraction curves according to one embodiment of the present invention.

Then in sub-operation 152, the sensitivity of the spectral diffraction measurements with respect to the selected set of measurement angles is determined. In one implementation, the sensitivity of the spectral diffraction measurements is determined through an integration method. The integration is performed on spectral diffraction curves generated by the spectroscopic model. Specifically, the integral is taken along a range of wavelengths and between two values for the variable of interest. The two variable values will typically encompass a likely value of the variable to be measured on the sample. FIG. 4 will now be described to present a graphical view of this integral.

FIG. 4 illustrates a two-dimensional coordinate system 200 that contains two theoretical spectral diffraction curves 202 and 204, according to one embodiment of the present invention. The coordinate system 200 includes a horizontal axis that represents a range of wavelengths, λ, and a vertical axis that represents a range of Intensity values. Each spectral diffraction curve 202 and 204 spans a range of wavelengths and varies in its Intensity value. The spectral diffraction curves 202 and 204 represent the spectral diffraction profile generated by the spectroscopic model based upon a defined sample, at the selected set of measurement angles. Each of curves 202 and 204 differ in that each curve is generated based upon a different variable value. Each variable value, respectively, represents the endpoints of a range that typically encompasses the likely variable value on the sample to be measured. In this way, the desired angle will have a high sensitivity for the variable to be measured. It should be understood that each variable value represents the limits for evaluating an integral of the curves.

The crosshatched area represents the integrated region 206 that lies between the curves 202 and 204. The integrated region 206 corresponds to the sensitivity of the set of selected measurement angles with respect to varying values of the variable of interest. A large region 206 corresponds to a large difference in the spectral diffraction profile when the value of the variable of interest changes in value and therefore a high sensitivity to the variable of interest. On the other hand, a small region 206 corresponds to a small difference in spectral diffraction profile when the variable of interest changes in value and therefore a low sensitivity to the variable of interest.

The intensity measured along the vertical axis of the coordinate system 200 can correspond to any reflectometric or ellipsometric spectra. For example, in one embodiment, the intensity is a polarized intensity, which requires two graphs wherein each graph is represents each polarization. The intensity can be defined according to various functions common in SE measurements. Intensity can also be quantified according to a ratio of two intensities corresponding to two orthogonal polarization states (e.g., the so-called s-polarized and p-polarized light).

At decision block 154, a decision is made as to whether the sensitivity of the spectral diffraction measurements is to be measured with respect to an additional set of measurement angles. Typically, the sensitivity of the spectral diffraction measurements will be measured with respect to multiple sets of measurement angles so that the degree of sensitivity at each set of measurement angles can be compared. Therefore, a "yes" decision will commonly be made at block 154 to repeat operations 150 and 152. When the sensitivity to a variable of interest has been determined after a satisfactory number of iterations, a "no" decision at block 154 allows the execution of the process to proceed to sub-operation 156.

At sub-operation 156, a desired set of measurement angles is selected. The selection is made by comparing the sensitivity of the spectral diffraction measurements measured in sub-operation 152. In other words, the integrals evaluated in operation 152 are compared against each other. In one embodiment, the set of measurement angles with the largest sensitivity, which corresponds to the largest integral, is selected as the desired set of measurement angles.

In some embodiments, the set of measurement angles that results in the highest signal-to-noise ratio will be selected as the desired set of measurement angles.

After sub-operation 156, a decision is made at decision block 158 as to whether a desired set of measurement angles for another sample variable should be determined. If an additional desired set of measurement angles is to be determined, the execution of the sub-operations of operation 104 returns to sub-operation 150. For example, the first progression through the sub-operations of operation 104 can determine the desired set of measurement angles for a height of a feature on the sample and then a second progression can be performed to determine the desired set of measurement angles for a width of the same feature. When no additional sets of desired measurement angles are to be determined, the execution of the process proceeds to operation 106.

When selecting a new set of measurement angles in sub-operation 150, after a "yes" decision at decision block 158, each newly selected set of measurement angles can have a new azimuth angle and the same polar angle, or vice-versa. Alternatively, a new set of measurement angles can be selected to have both a new azimuth and polar angle.

An alternative implementation of sub-operation 152, involves determining the sensitivity of the spectral diffraction measurements by determining the derivative of a function that defines a spectral diffraction curve. For example, with respect to curve 202 of FIG. 4, the derivative of the function that defines curve 202 is taken as the value of the variable of interest increases through a range of values. The curve 202 is defined at one set of measurement angles. The range of values of the variable of interest should encompass an expected variable value so that the desired set of angles will have a high sensitivity for the variable to be measured. After at least one "yes" decision at decision block 154, the derivative of a spectral emission curve is evaluated at least more than one set of measurement angles. Then during sub-operation 156, a set of measurement angles corresponding to, for example, the largest derivative of a spectral diffraction curve is selected as the desired set of measurement angles. The largest derivative indicates a very sensitive set of measurement angles because the rate of change of a spectral curve changes most rapidly.

Alternative techniques for determining a set of desired measurement angles can also be implemented. The techniques applied can depend upon the set of measurement angles that is desired as different techniques can be used to determine the most effective measurement angles for different measurement goals.

Operation 106 involves adjusting the set of measurement angles of an incident beam in an SE system to the desired angles determined in operation 104. SE systems can be designed to adjust the set of measurement angles of an incident beam using various system configurations involving for example, optical mirrors and lenses. Generally, the azimuthal angle, $\Phi$, is relatively easy to adjust as this can be accomplished by rotating the sample in the horizontal plane. For example, a semiconductor wafer sample can be rotated like a spinning disc to adjust the azimuthal angle. In some SE systems, the azimuth angle is set to zero by default. This means in the case of two-dimensional sample (gratings), the plane of incidence of the SE system is perpendicular to grating lines. By rotating the sample (or wafer) stage, we can adjust the relative angular position of this plane of incidence relative to the grating lines. In this way, we may find an optimum azimuth angle at which the sensitivity of SE system is maximized to on CD/profile variable, while the sensitivity to another CD/profile variable is minimized.

Figure 5:
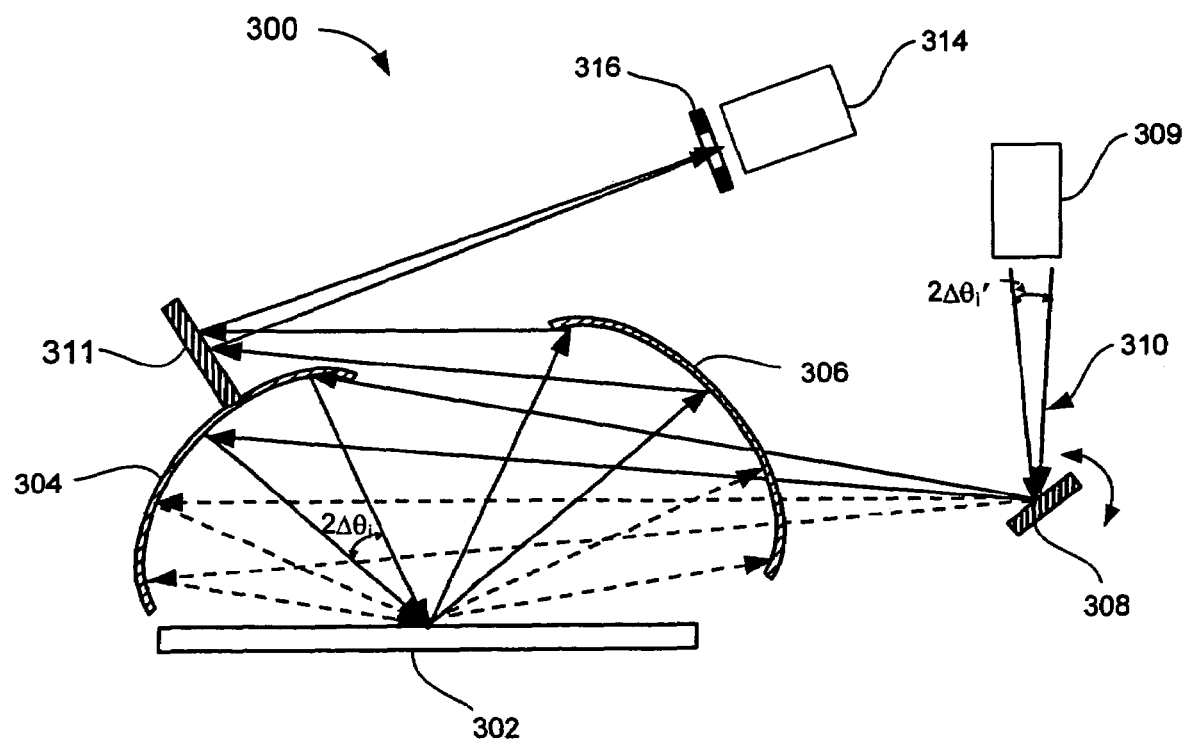
FIG. 5 illustrates an SE system having an incident beam that can be adjusted to be incident upon a sample at variable azimuth and polar angles, according to one embodiment of the invention.
Figure 6:
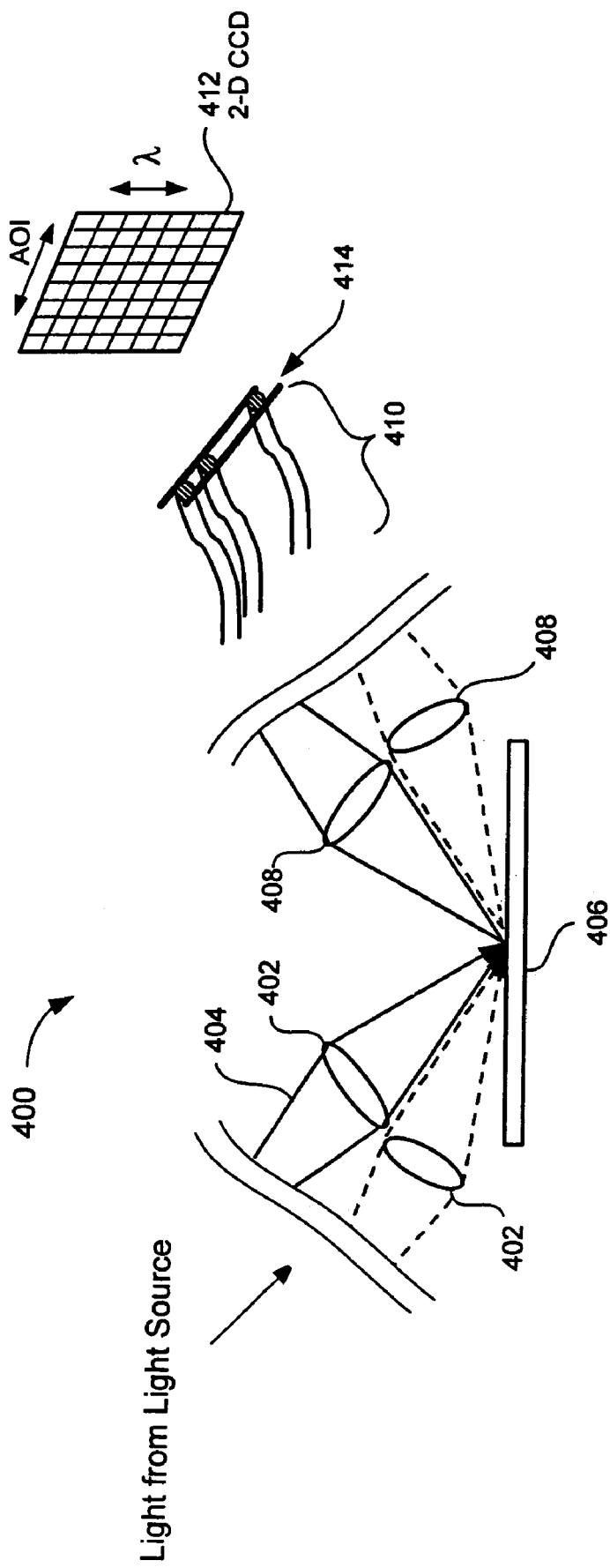
FIG. 6 illustrates an SE system that uses multiple objectives of a single high NA objective lens for multiple angle of incidence (AOI) SE measurements according to one embodiment of the invention.

The polar angle, $\theta$, can be relatively challenging to adjust however. In some embodiments, one of the azimuth or polar angles can be adjusted while the other angle is held at a single angle. In other embodiments, both the azimuth and the polar angle can be adjusted before an upcoming measurement process. FIGS. 5 and 6 will be described below to present exemplary SE systems that can adjust the azimuthal and polar angles of measurement.

Operation 108 involves performing the SE measurements on the sample. This involves directing the incident beam upon the sample at the desired set of measurement angles and measuring the spectral diffraction profile from the sample.

It should be understood, that commonly understood techniques for analyzing and deriving useful information from the spectral data collected in operation 108 can be used. One technique for determining the value of a measured variable involves matching the empirically collected spectral diffraction profile from the SE system against a theoretically generated spectral diffraction profile from the spectroscopic model. When a match is found between an empirical spectral diffraction profile and a theoretical spectral diffraction, then the variable values that correspond to the spectroscopic model are deemed to reflect the variable values of the sample. Conventional curve fitting techniques can be used to find a match between the empirical and the theoretical spectral diffraction profiles. Again, such variable values can correspond to the height, length, width, and sidewall angles of a feature, for example. It is noted that other analysis techniques and their details are not further described so that this discussion can focus upon the inventive aspects of the present invention.

As discussed earlier, the process 100 of FIG. 2 can be performed to determine a desired set of measurement angles for a single sample variable or multiple variables. For instance, the process can be run twice to find the most sensitive set of angles for a height and then for a width of a feature. The measurement operation 108 can then be run in various manners. In one embodiment, the measurement operation 108 measures the sample using the desired set of measurement angles for the width and then adjusts the set of measurement angles for the desired set of angles for measuring the height. However, in an alternative embodiment, a single set of measurement angles is used to measure both the height and the width of a feature wherein the single set of measurement angles is a weighted average of the desired measurement angles for each variable. In other words, the set of measurement angles is a weighted average of the two different desired sets of measurement angles. For example, the weighted average can weight each variable equally where the weighted average set of measurement angles is an average of the two desired sets of measurement angles. Alternatively, the weighted average of the desired sets of measurement angles can weigh one set of measurement angles completely without weighting the other set of measurement angles at all. Of course, any weighting combination can also be used depending upon the relative importance of each variable.

The techniques of the present invention pertain to determining desired sets of measurement angles in spectroscopic reflectometry and ellipsometry systems. Spectroscopic measurements typically involve measuring spectral diffraction profiles that span over a range of wavelengths.

Figure 7:
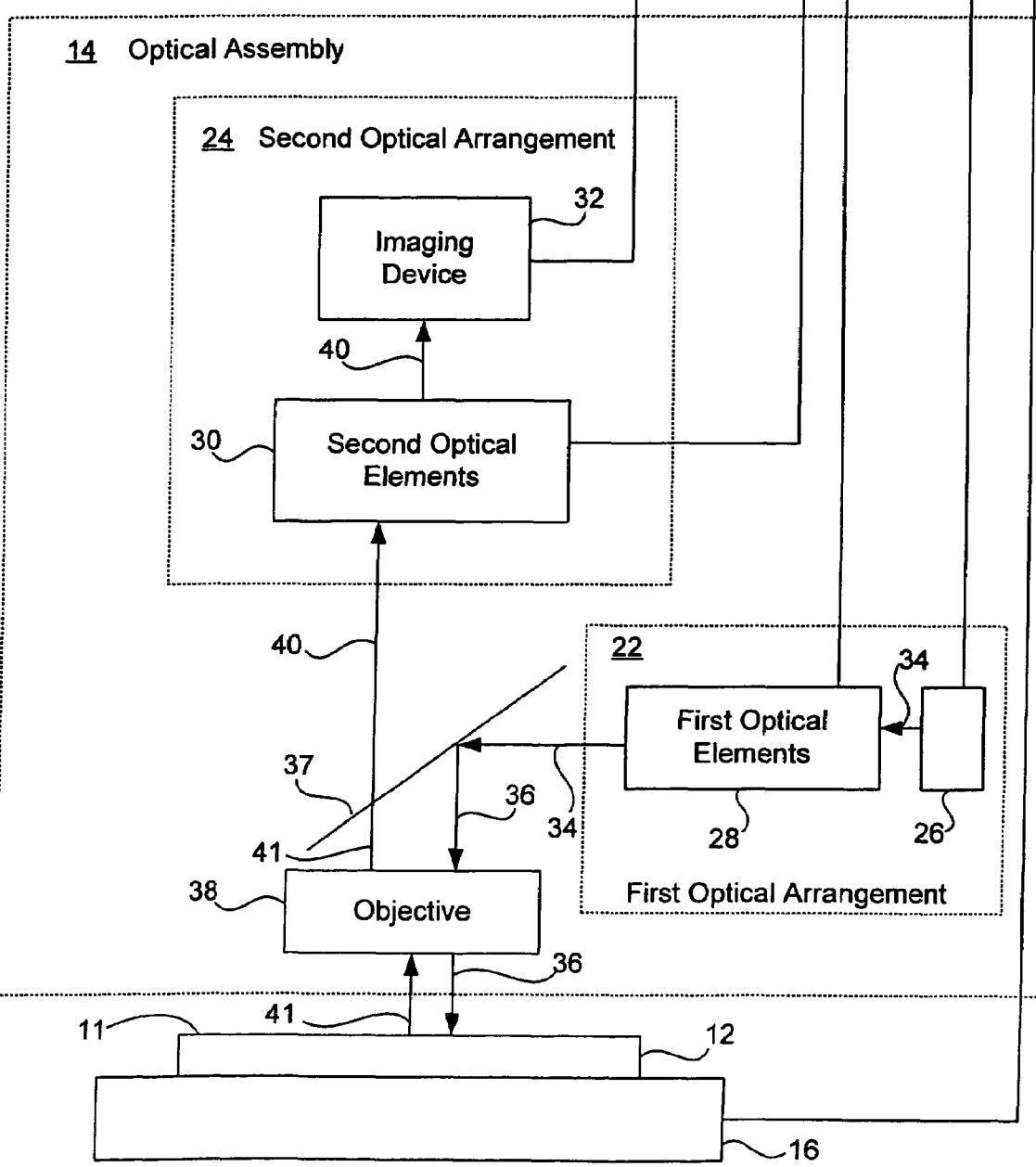
FIG. 7 is a simplified block diagram of an optical measurement system that may be used to implement embodiments of the present invention.

FIGS. 5-7 will be described to show several SE measurement systems that can adjust the measurement angle of an incident beam according to the techniques of the present invention.

FIG. 5 illustrates an SE system 300 having an incident beam that can be adjusted to be incident upon a sample 302 at variable azimuth and polar angles, according to one embodiment of the invention. In this embodiment, two ellipsoidal mirrors 304 and 306 are used for both focusing and collection purposes. The SE system 300 also includes a light source 309 that produces an illumination beam 310, a scanning mirror 308, a folder mirror 311, a collection aperture 316, and an analyzer or spectrometer 314.

Ellipsoidal mirror 304 serves as the focusing mirror and the ellipsoidal mirror 306 serves as the collection mirror. The variation of the polar angle is obtained by a scanning mirror 308, which rotates or tilts back-and-forth. The scanning mirror 308 is out of the plane of the ellipsoidal mirrors 304 and 306. Rotating the sample 302 in the horizontal plane can vary the azimuth angle.

In the illumination side, the key design feature is that the light spot on the scanning mirror 308 surface and the measurement spot on the surface of the sample 302 are the two foci of the focusing mirror 304. In addition, the focusing mirror 304 has a large numerical aperture (NA) and is underfilled. A light source 309 directs and illumination beam 310 upon the scanning mirror 308. In some embodiments, the light source 309 can be a polarized light source. The illumination beam 310 from the scanning mirror 308 has a NA that is significantly smaller than the NA of the focusing mirror 304. So at a given position of the scanning mirror 308, only part of the focusing mirror 304 is used to reflect the illumination beam 310 coming from the scanning mirror 308 onto the sample 302. The polar angle of the illumination beam 310 in reference to the sample 302 is then defined by the central ray of illumination beam 310 corresponding to this particular position of the scanning mirror 308. This relation between the position of scanning mirror 308 and the polar angle is illustrated in FIG. 5 by the solid lines.

To change the polar angle, only the scanning mirror 308 needs to be rotated to another position. As a result, another part of the focusing mirror 304 is used to reflect the illumination beam 310 onto the sample 302, and the polar angle, defined again by the central ray of the illumination beam 310, is changed accordingly, as it is illustrated in FIG. 5 by the dashed-lines.

Because the light spot on the scanning mirror 308 and the measurement spot are in conjugate and are the two foci of the focusing mirror 304, when the scanning mirror 308 rotates, the measurement spot will always remain in the same place. Because the collection aperture 316, the measurement spot on the sample 302 surface, and focus of the incident beam on the scanning mirror 308 are in conjugate, the detector or spectrometer 314 behind the collection aperture 316 will only pick up the desired light signal reflected from the sample 302 surface. In addition, the numeric aperture (NA) of the measurement system 300 is defined by the angular aperture of the measurement beam $2\Delta\theta_f$, as shown in FIG. 5, which in turn is defined by the part of the focusing mirror 304 illuminated by the incident beam coming from the scanning mirror 308. As a result, the NA of the measurement beam falling on the sample 302 surface is defined by the NA of the incident beam on the scanning mirror 308, i.e., the angular aperture $2\Delta\theta_i'$, as shown in FIG. 5.

A similar design is applied also to the collection side. Now the measurement spot and the entrance slit of the spectrometer 314 are in conjugate with the foci of the ellipsoidal collection mirror 306. As a result, when the polar angle changes, the position of the light spot on the entrance slit of the spectrometer 314 will not move.

The advantages of this embodiment include that only one movement is needed to vary the polar angle. Also the system 300 has high stability since the use of ellipsoidal mirrors for focusing and collection ensures that there is neither measurement spot displacement nor movement of the light spot on the entrance slit of the spectrometer 314. Furthermore, the SE system design enables accurate and stable polar angle calibration and optical calibration. Additionally, the SE system 300 has high efficiency in power utilization.

FIG. 6 illustrates an SE system 400 that uses multiple objectives of a single high NA objective lens for multiple angle of incidence (AOI) SE measurements according to one embodiment of the invention. SE system 400 uses two focusing lenses 402 for focusing the illumination beams 404 onto the same measurement spot on the surface of the sample 406, and two collection lenses 408 are used to pick up the beams reflected from the surface of the sample 406. Illumination beams 404 are directed from an illumination source (not shown). In one implementation of this embodiment, the SE system 400 is not limited to the multiple-lens scheme and not limited to two lenses on both the illumination and the collection sides. One may use many lenses, as far as the space in the system 400 can allow. In addition, it is also not limited to lenses. One may use multiple mirrors for either the focusing or the collection, or for both purposes. Furthermore, this embodiment is even not limited by the multiple lenses/mirrors arrangement. One may use, for example a high NA lens or mirror, containing a range of angles of incidence.

The common feature in all these various arrangements of using multiple lenses/mirrors or high NA lenses/mirrors is the use of an optical fiber bundle 410 to revolve the angle of incidence. In the case of multiple lenses/mirrors, each fiber in the optical fiber bundle 410 will pick up the reflected beam corresponding one lens or mirror, with the angle of incidence defined by the principle ray passing through the lens or reflected by the mirror. When a high NA lens or mirror is used, each fiber in the optical fiber bundle 410 will collect a portion of the reflected beam, with the angle of incidence defined by the central ray of this collected beam.

To resolve the spectra, one needs to use a spectrometer with dispersive elements such as a grating, for instance. The key to resolve both the angles of incidence and the spectra is the arrangement of the optical fiber bundle 410 on the entrance slit of a spectrometer 412. As it is illustrated in FIG. 6, the terminals of the optical fiber bundle 410 facing the spectrometer 412 are arranged into a rectangular, elongated array, with the long size parallel to the entrance slit 414 of the spectrometer 412. As a result, each terminal on the entrance slit 414 of the spectrometer 412 corresponds to a specific angle of incidence. When a grating is used as the dispersive element, the slit is arranged parallel to the grating lines. As a result, a single beam of the light coming out of each fiber will be dispersed, separated into beams of various wavelengths. To receive this multitude of signals with various angles of incidence and wavelengths, a two-dimensional image array is used, as again illustrated in FIG. 6. The rows of the image array are in the direction parallel to the entrance slit of the spectrometer 412, and the columns are in the direction of dispersion. As a result, the angles of incidence are resolved by the pixels in the row, while the wavelengths are resolved in the pixels in the columns.

There are many advantages to SE system 400. For one, SE system 400 is capable of resolving both angles of incidence and wavelengths without overlap and resolution degradation. Also, a large percentage of the power available to the SE system 400 is effectively utilized since all the illumination beams are located in the plane of incidence corresponding to zero azimuth angle and no portion of the illumination beam is lost. Also, there are no moving parts to SE system 400. This gives the SE system 400 high stability and a capability to obtain stable and accurate angle of incidence calibration. Furthermore, SE system 400 has high-throughput because of the capability of obtaining angle of incidence and wavelength information simultaneously.

The following describes a method for using SE systems, such as in FIGS. 5 and 6, for measuring sample variables. The method involves optimizing angles of incidence for specific sample structures, instead of using variable angles of incidence (AOI) or multiple angles of incidence described above. For instance, for a given application with specifically defined pattern structures and underlayer materials and thicknesses, a spectral CD measurement system may show the highest level of sensitivity to middle CD (MCD) at one $AOI=AOI_1$, while the AOI for the highest level of sensitivity to a side wall angle (SWA) may be found at another value $AOI=AOI_2$. In addition, it is possible to find that at another $AOI=AOI_3$, the spectral CD measurement system is the least sensitive to SWA, while in the meantime, the sensitivity to MCD is still pretty high. Now suppose MCD and SWA are correlated. We may effectively reduce the level of correlation by setting the AOI of the measurement system at $AOI=AOI_3$, at which MCD can be measured accurately, while fixing the SWA at the nominal value. Because the sensitivity of the measurement system to SWA is minimized, this fixed value of SWA will not impact the accuracy of MCD measurement. In the next step, if SWA needs to be measured at a high level of accuracy, the AOI may simply be set to value $AOI=AOI_2$. Because the MCD has already been accurately measured, it can be fixed. These optimized values of AOI depend on the sample structures of a specific given application. For another application, the above procedures may be repeated to optimize the AOI in a similar way. This embodiment can use the SE system 300 of FIG. 5, in which the optimum AOI is set by turning the scanning mirror 308, or the SE system 400 of FIG. 6, in which the optimum AOI is utilized by using the illumination and collection channels corresponding to the optimum AOI.

To implement this method, two CD/profile variables that exhibit a high level of correlation are needed. Then a decision is made as to which variable is to be fixed. Next, an optimum AOI value is found at which the sensitivity to this fixed CD/profile variable is minimized. There are many advantages to this methodology. For example, the method is capable of reducing CD/profile variable correlation without requiring multiple AOIs.

Yet another embodiment of an SE system capable of adjusting the measurement angle of an incident beam uses multiple-head capability. For instance, such an SE system includes two sub-systems, a deep UV (DUV) spectroscopic ellipsometer (DUV SE), with spectral range from 190-300 nm, and a UV SE in the range of 220-800 nm. Both SE systems operate at two different AOIs. This multiple-head system configuration provides additional capabilities to reduce CD/profile variable correlation. The SE system can be optimized for one of the AOIs or both in order to reduce correlation. For instance, suppose that two CD/profile variables, MCD and SWA, are highly correlated. By finding a desired AOI according to a method of the present invention, desired AOIs can be found and set for each sub-system at which the sensitivity to one of the CD/profile variables is minimized. For instance, the AOI can be set to $AOI_1$ for the DUV SE such that the sensitivity of the DUV SE to MCD is minimized, while the sensitivity to MCD is still considerably high. Similarly, AOI can be set to $AOI_2$ for the UV SE such that the sensitivity of UV SE to SWA is minimized, while the sensitivity to SWA is still considerably high. In this way, the DUV SE will measure SWA with high accuracy, regardless of the MCD being fixed to the nominal value, and UV SE will measure MCD with high accuracy with fixed SWA. Alternatively, only one of the AOIs can be set, for example, the AOI for UV SE can be set to $AOI_2$ at which the sensitivity of UV SE to SWA is minimized. In this way, first we may use UV SE to measure MCD, and then use DUV SE to measure SWA, with MCD fixed to the value determined by UV SE.

This embodiment it is not limited to a system that contains two of the same sub-systems, such as two SEs. Any two sub-systems can be combined. For instance, one SE system may include a spectroscopic reflectometer, the dual-beam spectrometer (DBS), and a UV SE. Still in another combination, the SE system can include two sub-systems such as a single wavelength ellipsometer (SWE) and a SE.

Furthermore, it is understood that the SE system is not limited by a combination of two sub-systems. It may include any combination of two or more sub-systems. For instance, an SE system can include three sub-systems: a DUV SE; a DBS; and a UV SE. In general, this embodiment uses a method for optimizing one of the AOIs, or a combination of two or more AOIs, in an SE system that includes two or more sub-systems.

Another SE system upon which the present invention can be implemented is a modification of an SE system disclosed in U.S. Pat. No. 5,889,593 (the '593 patent), assigned to KLA-Tencor Technologies Corporation, which is hereby incorporated by reference for all purposes. Generally, the SE system disclosed in the '593 patent makes measurements with light rays at multiple measurement angles and at multiple wavelengths. The present invention can be implemented, for ex ample, by adding a monochrometer to the SE system of the '593 patent. A monochrometer, such as a grating, filter wheel, or a prism, allows only specific wavelengths of light to pass through. The modified SE system can then make measurements at multiple measurement angles while using the monochrometer to select desired wavelengths or to progressively step through various wavelengths.

FIG. 7 is a simplified block diagram of an optical measurement system 10 that may be used to implement embodiments of the present invention. Modifications to the optical measurement system 10 may be made to adjust the measurement angle (i.e., the azimuth angle and the polar angle) of the incident beam, which is referred to as the incident beam 36.

The optical measurement system 10 is arranged for measuring a surface 11 of a substrate 12. The dimensions of various components are exaggerated to better illustrate the optical components of this embodiment. As shown, the optical measurement system 10 includes an optical assembly 14, a stage 16, and a control system 17. The optical assembly 14 generally includes at least a first optical arrangement 22 and a second optical arrangement 24. In general terms, the first optical arrangement 22 generates a illumination beam incident on the substrate, and the second optical arrangement 24 detects a illumination beam emanating from the sample as a result of the incident illumination beam. The first and second optical arrangement may be arranged in suitable manner in relation to each other. For example, the second optical arrangement 24 and the first optical arrangement 22 may both be arranged over the substrate surface 11 so that reflected illumination beam resulting from incident illumination beam generated by the first optical arrangement 22 may be detected by the second optical arrangement 24. Several embodiments of the optical assembly 14 altered to implement the present invention are described further below with reference to FIG. 9.

In the illustrated embodiment, the first optical arrangement 22 is arranged for generating an illumination spot (not shown) on the surface 11 of the substrate 12. On the other hand, the second optical arrangement 24 is arranged for collecting reflected light that is produced by the illumination spot on the surface 11 of the substrate 12.

To elaborate further, the first optical arrangement 22 includes at least a light source 26 for emitting a light beam 34 and a first set of optical elements 28. The first set of optical elements 28 may be arranged to provide one or more optical capabilities including, but not limited to, directing the light beam 34 towards beam splitter 37 and through objective 38 to intersect with the surface 11 of the substrate 12. A portion of the incident beam 34 is reflected by beam splitter 37 and becomes incident beam 36 which is focused by objective 38 to a illumination spot (not shown in FIG. 1) on the surface 11 of the substrate 12.

Furthermore, the second optical arrangement 24 includes at least a second set of optical elements 30 and an imaging device 32. The second set of optical elements 30 are in the path of a collected light beam 40, which is formed after the incident light beam 36 intersect with the surface 11 of the substrate 12. The collected light beam 40 may result from reflected light beam 41 that is reflected off the surface 11 of the substrate 12. A portion of the reflected beam 41 passes by beam splitter 37 and becomes collected beam 40. The second set of optical elements 30 are adapted for collecting the collected light beam 40 and for forming an image of a portion of surface 11 of substrate 12 on the imaging device 32. The imaging device 32 is arranged for detecting the light intensity distribution of the collected light beam 40, and more particularly for detecting distribution in the intensity of light caused by the intersection of the incident light beam with the substrate. The imaging device 32 is arranged for detecting the light intensity distribution of the image and for generating signals based on the detected light.

With regards to the stage 16, the stage 16 is arranged for moving the substrate 12 within a single plane (e.g., x & y directions) and relative to incident beam 36, so that all or any selected part of the substrate surface 11 may be measured by the illumination spot.

The control system 17 generally includes a control computer 18 and an electronic subsystem 19. Although not shown, the control system 17 may also include a keyboard for accepting operator inputs, a monitor for providing visual displays of the measured substrate (e.g., defects), a database for storing reference information, and a recorder for recording the location of defects. As shown, the control computer 18 is coupled to the electronic subsystem 19. The electronic subsystem 19 is coupled to various components of the optical measurement system 10, and more particularly to the stage 16 and the optical assembly 14 including the first optical arrangement 22 and the second optical arrangement 24.

The control computer 18 may be arranged to act as an operator console and master controller of the system 10. By way of example, commands may be issued to and status may be monitored from all other subsystems so as to facilitate completion of operator assigned tasks. Additionally, the electronics subsystem 19 may also be configured to interpret and execute the commands issued by control computer 18. The configuration may include capabilities for, but not limited to, digitizing the input from imaging devices, compensating these readings for variations in the incident light intensity, constructing a virtual image of the substrate surface based on the detected signals, detecting defects in the image and transferring the defect data to the control computer 18, accumulating the output of the interferometers used to track the stage 16, providing the drive for linear motors that move the stage 16 or components of the optical assembly 14, and monitoring sensors which indicate status. Control systems and stages are well known in the art and for the sake of brevity will not be discussed in greater detail. A representative stage, as well as a representative controller, may be found in U.S. Pat. No. 5,563,702, which is herein incorporated by reference. It should be understood, however, that this is not a limitation and that other suitable stages and control systems may be used.

In most of the defect detection operations a comparison is made between two images. By way of example, the comparison may be implemented by the electronic subsystem 19 of FIG. 7. Broadly speaking, the imaging device 32 generates images, which are based on the measured light intensity distribution, and sends them to the electronic subsystem 19. The electronic subsystem 19, after receiving the images, compares the target images with reference images, which are either stored in a database or determined in a current or previous measurement.

In die-to-die measurement mode, two areas of the substrate having identical features are compared to each other and any substantial discrepancy is flagged as a defect. In the die-to-database measurement mode, a defect is detected by comparing the die under test with corresponding graphics information obtained from a computer aided database system from which the die was derived.

While this invention has been described in terms of several preferred embodiments, there are alteration, permutations, and equivalents, which fall within the scope of this invention. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

We claim:

1. A method for measuring a sample comprising:
defining a spectroscopic measurement model of the sample for calculating a theoretical characteristic of diffracted light from the sample based on a plurality of sample variables and a plurality of sets of measurement angles for an incident light upon the sample;
determining a set of desired measurement angles to be used for a spectroscopic measurement system, wherein the determination is accomplished by using the spectroscopic measurement model so that the set of desired measurement angles result in a calculated theoretical characteristic of diffracted light that is most sensitive to at least one of the sample variables as compared to other sets of measurement angles;
after determining the set of desired measurement angles, directing an incident beam of the spectroscopic measurement system upon the sample at the desired set of measurement angles, wherein the incident beam causes a release of energy from the sample in the form of diffracted light; and
measuring the diffracted light from the sample.

2. A method as recited in claim 1 wherein the set of desired measurement angles includes a desired azimuthal angle and a desired polar angle.

3. A method as recited in claim 1 wherein the at least one of the sample variables includes a height, width, and/or sidewall angle of a feature on the sample.

4. A method as recited in claim 1 further comprising:
matching the diffracted light that is measured from the sample with a theoretical diffracted light generated by the spectroscopic measurement model; and
determining the value of the at least one sample variable to be equal to a theoretical sample variable that corresponds to the theoretical diffracted light.

5. A method as recited in claim 1 wherein determining the set of desired measurement angles is accomplished by evaluating an integral or derivative of the diffracted light over a range of wavelengths as calculated by the model for each of a plurality of measurement angle sets from which the set of desired measurement angles is determined as corresponding to the largest integral or derivative.

6. A method as recited in claim 5 wherein the set of desired measurement angles is determined so that the set of desired measurement angles results in a calculated theoretical characteristic of diffracted light that is most sensitive to a certain sample variable.

7. A method as recited in claim 5, wherein the set of desired measurement angles is determined so that the set of desired measurement angles results in a calculated theoretical characteristic of diffracted light that is most sensitive to a plurality of sample variables.

8. A method as recited in claim 5, wherein the operation of determining the set of desired measurement angles further comprises:
selecting a first set of measurement angles;
evaluating a first integral of the diffracted light along a range of wavelengths between a first variable value and a second variable value as calculated by the spectroscopic measurement model for the first set of measurement angles;
selecting a second set of measurement angles;
evaluating a second integral of the diffracted light along a range of wavelengths between the first variable value and the second variable value as calculated by the spectroscopic measurement model for the second set of measurement angles; and
determining as the set of desired measurement angles, either the first or second set of measurement angles which corresponds to the larger of the first integral and the second integral.

9. A method as recited in claim 5, wherein the operation of determining the set of desired measurement angles further comprises:
determining a first theoretical diffracted light at a first set of measurement angles using the spectroscopic measurement model;
evaluating a derivative of a function of the first theoretical diffracted light;
determining a second theoretical diffracted light at a second set of measurement angles using the spectroscopic measurement model;
evaluating a derivative of a function of the second theoretical diffracted light;
determining as the set of desired measurement angles, either the first or second set of measurement angles which corresponds to the larger of the derivatives of the functions of the first theoretical diffracted light and the second theoretical diffracted light.

10. A method as recited in claim 8 further comprising:
designating the first set of measurement angles as the set of desired measurement angles when the first integral is larger than the second integral; and
designating the second set of measurement angles as the set of desired measurement angles when the second integral is larger than the first integral.

11. A method as recited in claim 9 further comprising:
designating the first set of measurement angles as the desired measurement angle when the derivative of the function for the first theoretical diffracted light is larger than the derivative of the function of the second theoretical diffracted light; and
designating the second set of measurement angles as the desired measurement angle when the derivative of the function for the second theoretical diffracted light is larger than the derivative of the function of the first theoretical diffracted light.

12. A method for measuring a sample comprising:
defining a spectroscopic measurement model of the sample for calculating a theoretical characteristic of diffracted light from the sample based on a plurality of sample variables and a plurality of sets of measurement angles for an incident light upon the sample;
determining a set of desired measurement angles to be used for a spectroscopic measurement system, wherein the determination is accomplished by using the spectroscopic measurement model so that the set of desired measurement angles result in a calculated theoretical characteristic of diffracted light that is most sensitive to at least one of the sample variables as compared to other sets of measurement angles;
after determining the set of desired measurement angles, directing an incident beam of the spectroscopic measurement system upon the sample at the desired set of measurement angles, wherein the incident beam causes a release of energy from the sample in the form of diffracted light;
measuring the diffracted light from the sample;
repeating the determining operation to determine a subsequent set of desired measurement angles; and
adjusting the incident beam to the subsequent set of desired measurement angles.

13. A spectroscopic measurement system for measuring a sample comprising:

a spectroscopic measurement model of the sample for calculating a theoretical characteristic of diffracted light from the sample based on a plurality of sample variables and a plurality of sets of measurement angles for an incident light upon the sample;

a first analysis module that is configured to use the spectroscopic measurement model to determine a set of desired measurement angles for the spectroscopic measurement system so that the set of desired measurement angles result in a calculated theoretical characteristic of diffracted light that is most sensitive to at least one of the sample variables as compared to other sets of measurement angles;

an incident beam generator arranged to direct an incident beam towards the sample at the set of desired measurement angles after determining the set of desired measurement angles, wherein the incident beam causes a release of energy from the sample in the form of diffracted light; and a plurality of detectors arranged to measure the diffracted light from the sample.

14. A spectroscopic measurement system as recited in claim 13 wherein the first analysis module is further configured to determine the set of desired measurement angles so that the set of desired measurement angles results in a calculated theoretical characteristic of diffracted that is most sensitive to a certain sample variable.

15. A spectroscopic measurement system as recited in claim 13 wherein the set of desired measurement angles includes a desired azimuthal angle and a desired polar angle.

16. A spectroscopic measurement system as recited in claim 13, wherein the incident beam generator is arranged to direct an incident beam towards a grating pattern target formed on a surface of the sample.

17. A spectroscopic measurement system as recited in claim 13 further comprising:

a second analysis module suitable for:

matching the diffracted light that is measured from the sample with a theoretical diffracted light generated by the spectroscopic measurement model; and determining the value of the at least one sample variable to be equal to a theoretical sample variable that corresponds to the theoretical diffracted light.

18. A spectroscopic measurement system as recited in claim 13, wherein the set of desired measurement angles is determined so that the set of desired measurement angles results in a calculated theoretical characteristic of diffracted light that is most sensitive to a plurality of sample variables.

19. A spectroscopic measurement system as recited in claim 13 wherein the first analysis module is further configured to determine the set of desired measurement angles by evaluating an integral or derivative of the diffracted light over a range of wavelengths as calculated by the model for each of a plurality of measurement angle sets from which the set of desired measurement angles is determined as corresponding to the largest integral or derivative.

20. A spectroscopic measurement system as recited in claim 19, wherein the first analysis module is further configured to:

select a first set of measurement angles, evaluate a first integral of the diffracted light along a range of wavelengths between a first variable value and a second variable value as calculated by the spectroscopic measurement model set for the first set of measurement angles;

select a second set of measurement angles;

evaluate a second integral of the diffracted light along a range of wavelengths between the first variable value and the second variable value as calculated by the spectroscopic measurement model for the second set of measurement angles; and determine as the set of desired measurement angles, either the first or second set of measurement angles which corresponds to the larger of the first integral and the second integral.

21. A spectroscopic measurement system as recited in claim 20 wherein the first analysis module is configured to:

designate the first set of measurement angles as the desired measurement angle when the first integral is larger than the second integral; and designate the second set of measurement angles as the desired measurement angle when the second integral is larger than the first integral.

* * * * *